United States Patent [19]

Loeb

[11] Patent Number: 4,590,946

[45] Date of Patent: May 27, 1986

[54] SURGICALLY IMPLANTABLE ELECTRODE FOR NERVE BUNDLES

[75] Inventor: Gerald E. Loeb, Clarksburg, Md.

[73] Assignee: Biomed Concepts, Inc., Clarksburg, Md.

[21] Appl. No.: 620,640

[22] Filed: Jun. 14, 1984

[51] Int. Cl.⁴ .......................... A61B 5/04; A61N 1/05
[52] U.S. Cl. .................................... 128/642; 128/784; 128/785
[58] Field of Search ............... 128/642, 734, 784–786, 128/419 C, 419 P

[56] References Cited

U.S. PATENT DOCUMENTS

| 3,654,933 | 4/1972 | Hagfors | 128/784 |
| 3,724,467 | 4/1973 | Avery et al. | 128/784 |
| 3,760,812 | 9/1973 | Timm et al. | 128/784 |
| 3,957,036 | 5/1976 | Normann | 128/642 |
| 4,046,141 | 9/1977 | DeLuca | 128/642 |
| 4,341,221 | 7/1982 | Testerman | 128/642 |
| 4,400,590 | 8/1983 | Michelson | 128/784 X |
| 4,462,401 | 7/1984 | Burgio | 128/785 X |

Primary Examiner—Lee S. Cohen

[57] ABSTRACT

A surgically implantable electrode system has been conceived which includes two or more electrical elements embedded in a helically wound substrate made of insulative material. The contact elements are connected to electrical lead-in conductors which are encased in the substrate and extend from a common end of the substrate to a contact element. The substrate is wound around a nerve or nerve bundle in helical fashion until the contact elements are positioned against the nerve or nerve bundle surface at the desired location. A membrane is wrapped around the substrate to insulate the electrode system, and the lead-in conductors are anchored to relieve strain on the electrode system.

13 Claims, 4 Drawing Figures

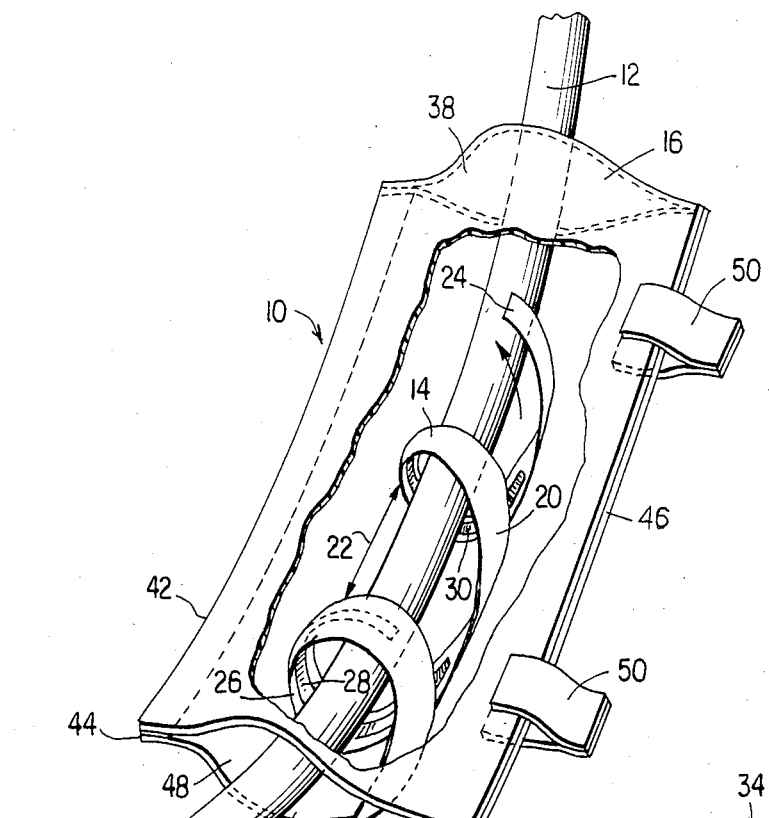
FIG. 1
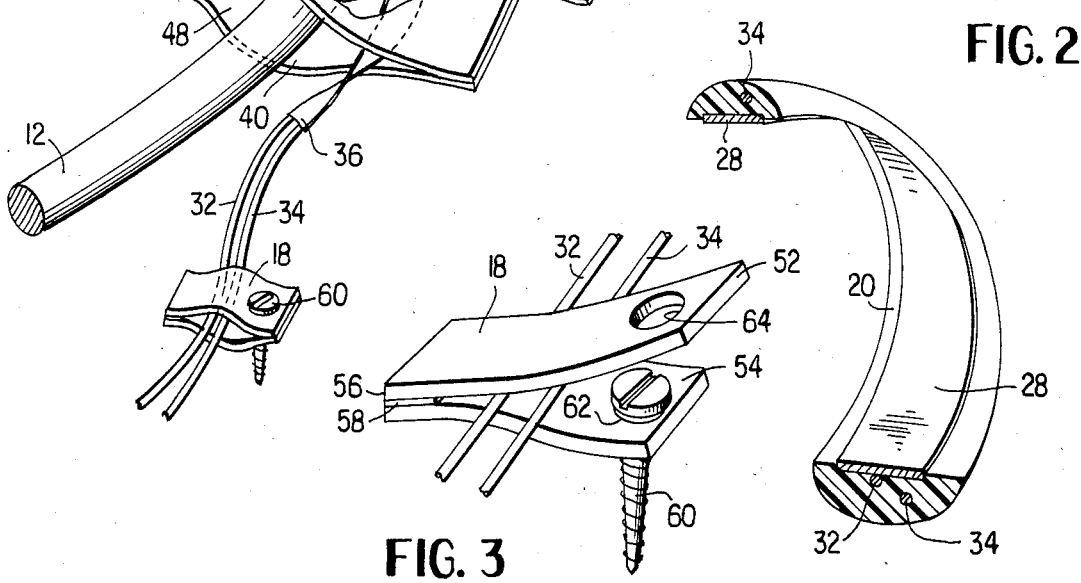
FIG. 2
FIG. 3
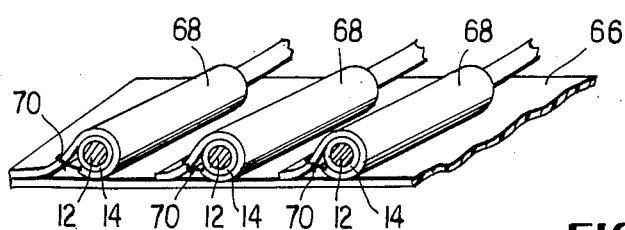
FIG. 4

SURGICALLY IMPLANTABLE ELECTRODE FOR NERVE BUNDLES

BACKGROUND, SUMMARY, AND OBJECTS OF THE INVENTION

This invention relates to electrode systems of the type that can be surgically implanted in the human body and attached to nerve bundles to provide electrical stimulation for those nerves and a means for recording electrical activity that occurs naturally in nerves.

The use of electrical currents to effect, control, and detect the activation of individual nerves constitutes an important tool for research on the function of the nervous system and for the treatment of neurological disorders stemming from paralysis, spasm, and other dysfunctional states of the organs innervated by such nerves. The clinical applications of electrically applied nerve stimulation include many of those that are the subject of current research in the field of neural prosthetics, including the functional electrical stimulation and blocking of peripheral nerves controlling the muscles of the arms and legs and the pelvic viscera such as the bladder and colon and their sphincteric muscles. Other applications of such an electrode include the recording of naturally occurring activity in intact nerves for purposes of obtaining motor control and sensory feedback signals.

In such applications, the efficiency and selectivity whereby a particular nerve bundle is recorded or stimulated, to the exclusion of surrounding nerves and other electrically active structures, depends on two separate electromechanical relationships. First, the electrode contacts which convey the electrical signals between the nerve and associated electronic circuitry must be positioned close to and surrounding the nerve bundles at two longitudinally spaced-apart positions. This causes the electrodes to detect or generate current flow along the axis of the nerve fibers comprising the bundle, in conjunction with natural propagation patterns which constitute the conducted action potentials of the individual nerve fibers. Second, the electrical fields in the vicinity of the nerve and the electrode contacts need to be confined to the longitudinal cylinder of the nerve itself, to prevent their dissipation by the volume conducting properties of the surrounding tissues and fluids.

Devices of the prior art have attempted to achieve both of these goals with cylindrical enclosures that completely or nearly completely surround the nerve and provide support for the electrode contacts and their attached electrical leads. This has caused such devices to be unnecessarily bulky, difficult to implant reliably, and prone to cause damage by compressing or kinking either the nerve or its associated blood supply or both of them. Furthermore, such devices must be carefully constructed to the dimensions of each anatomical configuration, and cannot be adapted or adjusted during surgery to cope with unexpected dimensions or configurations.

It is therefore the primary object of the present invention to provide a superior surgically implantable electrode system for providing electrical connection to a nerve bundle.

It is another object of the present invention to provide an effective method of attaching the electrode system to a nerve bundle during surgery without special instruments or techniques.

It is yet another object of the present invention to provide an implantable electrode system which, due to its unique construction, is easily adjusted by the surgeon at the time of implantation to accommodate nerves of any dimension or anatomical configuration and which provides precise and constant spatial relationships between the electrode contacts and the nerve bundle.

It is a further object of the present invention to provide an implantable electrode system which insures electrical isolation so that even closely adjacent, multiple sites of electrical recording or stimulation interact minimally.

It is a still further object of the present invention to provide an implantable electrode system whose physical properties and overall construction impose minimal trauma on the nerve and the device at the time of implantation, during the development of any scar tissue, and during movement of the device and the body parts in normal use.

The aforementioned objects of the present invention are accomplished by providing an electrode structure having a helically shaped insulative carrier or substrate with two or more electrical contacts imbedded on the inner-facing surface thereof. Electrical lead-ins are connected to the contacts and travel within the carrier to the end thereof where they exit as a bundle of wires running substantially parallel to the nerve bundle. This helical electrode structure can be slipped over the nerve by rotating it like a corkscrew. The pitch of this helix is more shallow and the turns more widely spaced than helical electrodes designed according to prior art, making the invention easier to apply and less damaging to delicate nerve bundles. For such a design to satisfy the object of stable, isolated electrical connection with the nerve bundle, separate means are provided as follows for confinement of electrical current around the nerve and electrode contacts and for strain relief of the electrical leads. The confinement of the electrical currents generated by or supplied to the nerve is accomplished by wrapping the nerve and the wound electrode structure in a thin, double layered, sheet or membrane of electrically nonconductive, flexible material such as silicone rubber. The layers can be closed by the use of conventional surgical sutures, staples, adhesive or the like. Strain relief of the electrode structure that would otherwise tend to drag on the nerve is accomplished by providing a slidable tab made of a stiff elastic material that can be clamped on the electrical leads. The tab frictionally engages the lead-in conductors and is attached to bone, fascia or other suitable connective tissue by screws, sutures, staples or other surgical fasteners. A plurality of electrode structures can be maintained in spaced apart relationship on a single, common base of insulative sheet or membrane material, having a plurality of separate covers of the same material, each adapted to enclose a separate electrode structure.

Other objects and advantages of the invention will appear in the following detailed description of the preferred embodiment of the invention as shown on the accompanying drawings.

IN THE DRAWINGS

FIG. 1 is a perspective view of the implantable electrode system of the present invention with the helical-shaped electrode shown in position on a nerve bundle.

FIG. 2 is a perspective view of a portion of the helical-shaped electrode of FIG. 1 shown in cross-section.

FIG. 3 is a perspective view of the strain relieving anchor of the present invention.

FIG. 4 is a perspective view of a portion of a plurality of the implantable electrodes of the present invention shown in spaced-apart relationship on a common base.

DETAILED DESCRIPTION OF THE INVENTION

Referring now to the drawings in which like characters of reference indicate like elements in each of the several views, numeral 10 in FIG. 1 refers generally to the surgically implantable electrode system of the present invention that provides an electrical connection to two or more locations on the elongated portion of a nerve bundle 12. The electrode system 10 comprises the three basic elements of an electrode 14, a wrapping material 16 and a strain relief anchor assembly 18.

The electrode 14 includes a carrier member or base 20 of an insulative elastic and biocompatible polymer material such as silicone rubber that has sufficient stiffness to maintain its helical shape during surgical manipulations necessary to position it around a nerve bundle 12. The carrier member 20 is preshaped or molded in a helical form which defines a spiral path or open space 22 within the helix. The carrier member 20 has a free end 24 and an inner-facing surface 26 containing, in the embodiment shown, electrical contact members 28, 30. The electrical contact members 28, 30, as can best be seen by referring to both FIGS. 1 and 2 are partially imbedded in the inner facing surface 26 of carrier member 20 in spaced apart relationship to each other. The contact members 28, 30 consist of a corrosion-resistant metal foil such as iridium, whose outer surface establish electrical contact with the outer surface of the nerve bundle 12. A larger number of independent contact members similar to 28, 30 each with precise surface area and orientation with respect to each other and to nerve bundle 12, can be imbedded in the carrier member 20 during its fabrication by molding or other suitable process.

Each of the contact members 28, 30 is connected to one end of each of two insulated lead-in electrical conductors 32, 34, respectively, which travel within and are encased by the carrier member 20. The other ends of the conductors 32, 34 exit the end 36 of the carrier member 20 adjacent the nerve bundle 12 and connect to electrical circuitry (not shown).

The confinement of the electric currents about the electrode 14 and nerve bundle 12 is accomplished by means of the wrapping membrane assembly 16 which is placed around both the helical electrode 14 and the nerve bundle 12. The wrapping assembly 16 comprises a first and second sheet or layer 38, 40 of thin, electrically nonconductive, flexible material such as silicone rubber. The layers 38, 40 are attached between the layers at one edge 42 by an adhesive layer 44. At the opposite edge 46, the layers 38, 40 may be closed over the nerve bundle 12 to create a sealed, substantially cylindrical enclosure 48 by means of clips 50 or by means of a pressure sensitive adhesive layer, surgical sutures or staples (not shown).

The completed wrapping assembly 16 thus described causes the electrical current applied between the electrode contacts 28, 30 to be concentrated in a path which is within and immediately surrounding the enclosed nerve bundle 12 and parallel to the longitudinal nerve fibers within the nerve bundle 12. By extending the length of the enveloping wrapping assembly 16 in both directions along the nerve bundle 12 beyond the locations of the electrode contacts 28, 30 the electrical current can be confined to a path which is within and immediately surrounding the enclosed nerve bundle 12 and parallel to the longitudinally extending nerve fibers within that bundle. By so lengthening the wrapping assembly 16 in both directions along the nerve bundle 12 beyond the locations of the electrode contacts 28, 30, the amount of current flow outside the cylindrical enclosure 48 created by the wrapping assembly 16 can be greatly reduced thereby preventing undesired effects in adjacent nerve bundles outside of the individual electrode system.

FIG. 3 shows the anchor assembly 18 which provides strain relief to the electrode 14 and prevents the conductors 32, 34 from tending to drag along the nerve bundle 12. The anchor assembly 18 consists of an upper layer 52 and a lower layer 54, both made of a somewhat stiffer elastic material such as silicone rubber, joined at one edge 56 by an adhesive layer 58. The anchor assembly 18 is secured to a bone screw 60 by first pressing an undersized hole 62 in the lower layer 54 over the rounded head of the screw 60. The two conductor wires 32, 34 are then inserted into the space between the upper and lower layers 52, 54, respectively, and locked into this space by friction when the hole 64, also undersized, is pressed over the head of screw 60. This manual attachment of the anchor over the head of a previously installed bone screw eliminate the danger of using drilling and screwdriving tools in the vicinity of the delicate electrode assembly and conductor lead-in wires. If suitable sites are not available for inserting screw 60, the layers 52, 54 of the anchor assembly 18 may be closed and anchored with surgical sutures, staples, pressure-sensitive adhesive, or other fasteners well known in the art. The upper and lower layers 52, 54 are shaped so as to grip the leads firmly but allow the surgeon to add, remove, or reposition one or more such anchors at the time of implantation.

Referring now to FIG. 4, another embodiment of the present invention is disclosed for use in one general location where several different nerve bundles 12 must each be attached to a plurality of electrodes 14 for individual and selective control by multiple, independent electrical circuits. In this embodiment, a single lower layer 66 of membrane material is provided to which separate upper layers 68 are attached by adhesive or other of the means previously described. Each upper layer 68 is wrapped around the electrode 12 and associated nerve bundle 12 to enclose them in separate, spaced-apart pockets. The upper layers 68 can be secured to themselves by a suitable means such as sutures 70 as shown. The multiple conductor leads extending from the plurality of electrodes 14 can be secured by the aforedescribed anchor assemblies 18 to provide strain relief for those leads. This and other simpler wrapping schemes using single layer materials may be suitable for situations in which only one nerve bundle must be instrumented or electrically stimulated.

Applicant has thus described in detail his implantable electrode system which employs the novel concepts of physical separation of the electrode contact positions, the electrode wrapping for electrical current confinement, and the strain relieving functions achieved by the anchor assembly.

It is apparent that many modifications and variations of this invention as hereinbefore set forth may be made without departing from the spirit and scope thereof.

The specific embodiments described are given by way of example only and the invention is limited only by the terms of the appended claims.

What I claim is:

1. A surgically implantable electrode system for providing electrical connection to a nerve bundle, said system comprising:
   (a) electrode means having a helically-shaped carrier member of insulative material adapted to be positioned around said nerve bundle, said electrode means having at least two contact elements on said carrier member for engagement with said nerve bundle and an electrical lead-in conductor member connected to each of said contact elements, and
   (b) membrane means for enclosing said electrode means to confine electrical currents passing through said electrode means to said nerve bundle.

2. A system as set forth in claim 1 wherein said insulative material of said carrier member is an elastic and biocompatible polymer such as silicone rubber.

3. A system as set forth in claim 1 wherein said contact elements are elongated strips of corrosion-resistant metal foil such as iridium.

4. A system as set forth in claim 1 wherein said electrical lead-in conductor members are encased within and extend from a common end of said carrier member to each respective contact element.

5. A system as set forth in claim 1 wherein said membrane means consists of a single layer of thin, flexible nonconductive material such as silicone rubber wrapped around said electrode means.

6. A system as set forth in claim 1 wherein said membrane means comprises an elongated base member of insulative material and a plurality of cover members secured to said base member along one edge thereof, in spaced-apart relationship to each other, each of said cover members being adapted to enclose a separate electrode means.

7. A surgically implantable electrode system for providing electrical connection to a nerve bundle, said system comprising:
   (a) electrode means having a helically-shaped carrier member of insulative material adapted to be positioned around said nerve bundle, said electrode means having at least two contact elements on said carrier member for engagement with said nerve bundle and an electrical lead-in conductor member connected to each of said contact elements,
   (b) membrane means for enclosing said electrode means to confine electrical currents passing through said electrode means to said nerve bundle, and
   (c) anchor means for securing said lead-in conductor members to relieve strain on said electrode means.

8. A system as set forth in claim 7 wherein said insulative material of said carrier member is an elastic and biocompatible polymer such as silicone rubber.

9. A system as set forth in claim 7 wherein said contact elements are elongated strips of corrosion-resistant metal foil such as iridium.

10. A system as set forth in claim 7 wherein said electrical lead-in conductor members are encased within and extend from a common end of said carrier member to each respective contact element.

11. A system as set forth in claim 7 wherein said membrane means consists of a single layer of thin, flexible nonconductive material such as silicone rubber wrapped around said electrode means.

12. A system as set forth in claim 7 wherein said membrane means comprises an elongated base member of insulative material and a plurality of cover members secured to said base member along one edge thereof, in spaced-apart relationship to each other, each of said cover members being adapted to enclose a separate electrode means.

13. A system as set forth in claim 7 wherein said anchor means comprises first and second strips of thin insulative material secured together at one end and having means at the other end for attachment to a fixed member, each of said lead-in conductor members being held between said strips when said attachment is achieved.

* * * * *